United States Patent [19]

Tamm

[11] 4,111,563
[45] Sep. 5, 1978

[54] GRAPHITE TUBE ASSEMBLY HAVING A SAMPLE SUPPORTING INNER BODY

[75] Inventor: Rolf Tamm, Salem, Fed. Rep. of Germany

[73] Assignee: Bodenseewerk Perkin-Elmer & Co., GmbH, Überlingen, Fed. Rep. of Germany

[21] Appl. No.: 746,970

[22] Filed: Dec. 2, 1976

[30] Foreign Application Priority Data

Dec. 6, 1975 [DE] Fed. Rep. of Germany ....... 2554950

[51] Int. Cl.² .......................... G01N 21/16; G01J 3/30
[52] U.S. Cl. ........................................ 356/244; 356/85
[58] Field of Search .................................. 356/85, 244

[56] References Cited

U.S. PATENT DOCUMENTS

| 3,862,805 | 1/1975 | Tamm ................................. 356/85 |
| 4,008,963 | 2/1977 | Huber et al. ........................ 356/85 |

OTHER PUBLICATIONS

"The Det. of Barium . . . Modified Graphite Tube Atomizer;" Renshaw; Atomic Absorption Newsletter, vol. 12#6; Nov-Dec. 1973; pp. 158-160.
"New Generation Flameless AA Atomizer;" Hwang et al.; Am. Labs; vol. 6#11; Nov. 1974; pp. 42-46.
"A Tantalum Foil-Lined Graphite Tube . . . ;" Baird et al.; Applied Spectroscopy; vol. 28#3; May/Jun. 1974, pp. 273-274.

Primary Examiner—Vincent P. McGraw
Attorney, Agent, or Firm—Salvatore A. Giarrantana; Francis L. Masselle; Edwin T. Grimes

[57] ABSTRACT

The invention relates to a graphite tube assembly for use in an atomic absorption spectrometer for measuring the flameless absorption of samples when passing a beam of radiation therethrough, which includes a graphite tube and an inner body disposed in the interior of the graphite tube, but externally of the beam of radiation when passing through the tube, said inner body extending only over a portion of the length of the graphite tube.

15 Claims, 3 Drawing Figures

GRAPHITE TUBE ASSEMBLY HAVING A SAMPLE SUPPORTING INNER BODY

BACKGROUND OF THE INVENTION

This invention relates to flameless atomic absorption spectroscopy, and more particularly the invention relates to a graphite tube assembly for use in measuring the flameless atomic absorption, particularly of liquid samples.

For atomic absorption measurements, it is conventional for a sample to be introduced into the interior of the graphite tube, dried at a relatively low temperature, ashed and, subsequently, atomized at a high temperature. The graphite tube is placed in the path of the rays of a spectrometer so that the absorption of light by the atoms present in the interior of the graphite tube can be measured.

It has been found that in measuring the atomic absorption of liquid samples disturbances may occur because the liquids spread out over wide portions of the inner wall of the graphite tube. The liquids also flow to the end portions of the graphite tube where there is incomplete evaporation, because of the relatively lower temperature thereat, so that the sample material is carried over and interferes with subsequent measurements of further samples. Because of the slightly porous structure of graphite, the sample may infiltrate the wall of the graphite tube to such an extent that an uncontrollable portion thereof will pass through the wall to the exterior when the tube is heated, and is thereby lost for the measurement. This results in substantially lowering the sensitivity of the measurement.

It is known, by virtue of German Offenlegungsschrift 23 23 774, that to avoid such problems the graphite tube may be provided with grooves, at least over a portion of its inner wall and extending transversely with respect to the tube axis. However, since the cutting of the grooves causes a substantial roughening of the inner face, additional infiltration of the sample material results therefrom, so that the improvement achieved does not reach the desired degree.

Further, it is known to manufacture graphite tubes of the aforementioned type from so-called pyrolytic graphite instead of from the usual graphite. This pyrolytic graphite is not porous and, therefore, is impervious to gases. Grooves may also be cut in the pyrolytic graphite without the sample infiltrating the walls of the tube. However, the use of pyrolytic graphite for this purpose is undesirable because of the high cost thereof.

SUMMARY OF THE INVENTION

With the foregoing state of the art in view, it is the primary general object of the invention to overcome or at least mitigate the problems and shortcomings of the devices outlined above.

A more specific object of the invention is to provide a new and improved graphite tube assembly for use in an atomic absorption spectrometer, which reduces the errors in measurement due to uninhibited spreading of the liquid sample over the inner wall of the graphite tube, which inhibits the infiltration of the liquid sample into the inner wall, and which is economical to fabricate because normal graphite may be employed.

To the accomplishment of the foregoing and/or other objectives, the invention contemplates the provision of a new and improved graphite tube assembly for use in an atomic absorption spectrometer for measuring the flameless absorption of samples when passing a beam of radiation or light rays therethrough, which includes in combination, a graphite tube and an inner body disposed in the interior of the graphite tube, but externally of the beam of light rays when passing through the tube, said inner body extending only over a portion of the length of the graphite tube.

According to one aspect of the invention, the inner body is made of graphite and is formed integrally with the graphite tube, and according to another aspect the inner body is spaced from the inner wall of the graphite tube and is connected therewith by means of webs. According to a further aspect of the invention, the inner body is of tubular configuration and has an inlet opening aligned with a sample introduction bore in the graphite tube by two diametrically opposed webs.

In one form of the invention, the inner body is of annular configuration, and the graphite tube has an introduction bore that extends through the inner body, and the inner body has a plurality of axially extending bores. Preferably, the inner body is connected to the inner wall of the graphite tube by webs between the axial bores.

As a feature of the invention, the inner body is provided with grooves transversely disposed with respect to the axis of the graphite tube on at least the portion of its inner surface facing the introduction bore in the assembly.

As another feature of the invention, the inner body has a gas impermeable lining on at least one portion of its inner surface facing the introduction bore in said graphite tube assembly. In one form thereof the gas impermeable lining consists of metal, preferably tungsten or tantalum, for example, which is secured to the inner body by a conventional shrink fit. In other forms thereof, the gas impermeable lining consists of a coating of pyrolytic graphite or ceramic material, for example. As still another feature of the invention, said gas impermeable lining has grooves transversely disposed with respect to the axis of the graphite tube on at least the portion of its surface facing the introduction bore.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which the disclosure is based may readily be utilized as a basis for the designing of other assemblies for carrying out the several purposes of the invention. It is important, therefore, that the claims be regarded as including such equivalent assemblies as do not depart from the spirit and scope of the invention.

Specific embodiments of the invention have been chosen for purposes of illustration and description, and are shown in the accompanying drawings, forming a part of the specification.

DETAILED DESCRIPTION OF THE PREFERRED EMBODIMENTS

Figure 1:
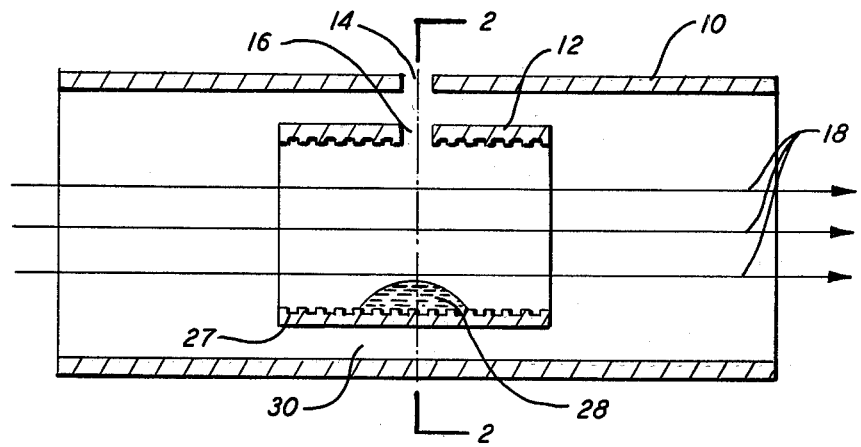
FIG. 1 is a medial, longitudinal, sectional view of a graphite tube assembly constructed in accordance with the concepts of this invention.
Figure 2:
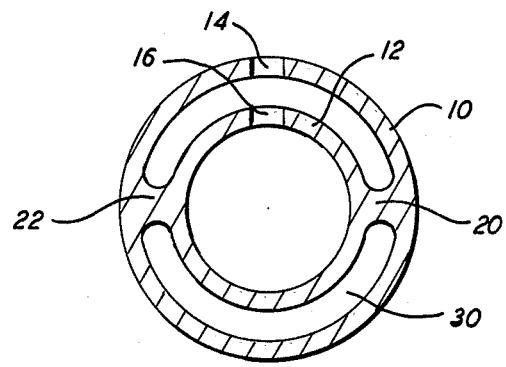
FIG. 2 is a transverse sectional view of the graphite tube assembly of FIG. 1 taken along the line indicated at 2—2 in FIG. 1.

In the embodiment of the invention illustrated in FIGS. 1 and 2, a graphite tube assembly comprises a graphite tube 10 mounted in the path of a beam of light rays, indicated by arrows 18, which pass therethrough for carrying out the atomic absorption measurements. A tubular shaped inner body 12 is mounted within the tube 10, and centered therein in such a way as to align its inlet opening 16 with the sample introduction bore 14 disposed in the wall of the graphite tube 10. It is noted that the inner body 12 only extends along a portion of the length of the graphic tube. A drop 28 of a liquid sample is placed in the interior of the inner body 12 for analysis. As best seen in the cross-sectional view of FIG. 2, the inner body 12 is formed integrally with the graphite tube and is connected to the inner wall thereof by two diametrically opposed webs 20, 22, so that an annular space 30 is formed therebetween to provide an unobstructed passage for the inert gas to flow through the tube.

Figure 3:
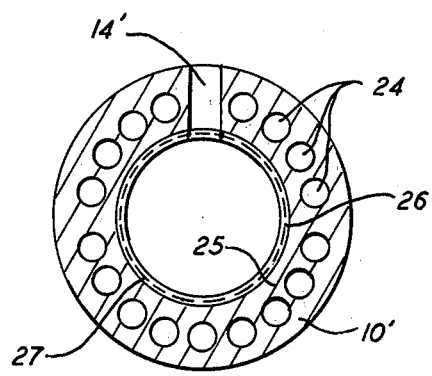
FIG. 3 is a transverse sectional view similar to FIG. 2, but showing another embodiment of the invention.

FIG. 3 shows another embodiment of the invention, which comprises an annularly shaped inner body 25 formed integrally with the graphite tube 10', through which a sample introduction bore 14' extends. There are axially extending bores 24 provided in the inner body 25 through which the inert gas flowing through the interior of the graphite tube 10' can pass unobstructed. It is noted that the annularly shaped inner body 25 is connected to the wall of the graphite tube 10' only through the webs existing between the axial bores 24.

It will be appreciated that the inner bodies 12 and 25 mounted in the graphite tubes 10 and 10', respectively, serve to restrict the spreading of the liquid sample, and even if the liquid penetrates the inner body per se it will not cause uncontrollable loss of that portion of the sample because what exits from the inner body due to evaporation will remain within the graphite tube 10, 10'. Further, because of the specially shaped inner body, the inert gas flow through the graphite tube 10, 10' remains practically unobstructed. A particular advantage of this device resides in the fact that the inner body is primarily indirectly heated and only directly heated to a small extent by the connecting webs to the graphite tube itself. As a consequence, its temperature, particularly during heating, will be somewhat lower than that of the surrounding graphite tube, resulting in a concentration of the atom cloud of the measuring sample within the region of the center of the graphite tube, which is particulary favorable for measurement.

The inner body may be fabricated from graphite and, as indicated hereinbefore, it is preferably formed integrally with the graphite tube. As best seen in FIG. 3, the inner wall of the inner body 25 is provided with a lining or coating of a material that is impervious to gases, thereby preventing penetration of the liquid sample into the wall material. For example, suitable materials for this lining include metals such as tungsten or tantalum, which may be applied to the inner body by means of a conventional shrink fit process. Alternatively, the lining may comprise a coating of pyrolytic graphite or a ceramic material, in some installations. Additionally, the inner surface, and especially the portion thereof facing the sample inlet, of the inner bodies 12 and 25 or the lining 26 preferably is provided with grooves 27 extending transversely with respect to the tube axis.

It will be appreciated that it is within the concept of this invention to provide inner bodies of configurations other than those describe hereinbefore in connection with the embodiments of FIGS. 1 and 3, such as a boat-like configuration or even a flat shaped body, for example. Inner bodies encompassing such other configurations may also be provided with linings and/or corrugated or grooved faces on their inner walls if desired for particular installations. It is necessary, however, that the inner bodies be so arranged that there is no interference with the passage of the light beam passing through the graphite tube and so as not to obstruct the flow of gas therethrough.

It will thus be seen that the present invention does indeed provide a new and improved graphite tube assembly for use in an atomic absorption spectrometer, which is substantially superior to prior art such devices. Having thus described the invention with particular reference to the preferred forms thereof, it will be obvious to those skilled in the art to which the invention pertains, after understanding the invention that various changes and modifications may be made therein without departing from the spirit and scope of the invention, as defined by the claims appended hereto.

What is claimed is:

1. A graphite tube assembly for use in an atomic absorption spectrometer for measuring the flameless absorption of samples when passing a beam of light rays therethrough comprising, in combination:
   a graphite tube, and
   a sample supporting inner body, means mounting said inner body in the interior of the graphite tube to form an integral structure with the inner body spaced from the inside wall of said tube, but externally of the beam of light rays when passing through said graphite tube, said inner body extending only over a portion of the length of the graphite tube.

2. A graphite tube assembly according to claim 1 wherein said inner body is made of graphite and is formed integrally with the graphite tube.

3. A graphite tube assembly according to claim 2 wherein said means mounting said inner body comprises radial stationary webs.

4. A graphite tube assembly according to claim 3 wherein said inner body is of tubular configuration and has a inlet opening aligned with a sample introduction bore in said graphite tube, and wherein said inner body is connected to the graphite tube by two diametrically opposed webs.

5. A graphite tube assembly according to claim 2 wherein said inner body is of annular configuration, and wherein said graphite tube has an introduction bore that extends through said inner body, and wherein the space between said inner body and said graphite tube is in the form of a plurality of axially extending bores.

6. A graphite tube assembly according to claim 5 wherein the inner body and the graphite tube is fabricated from a single solid member.

7. A graphite tube assembly according to claim 1 wherein said inner body is of hollow cylindrical configuration and has grooves transversely disposed with respect to the axis of the graphite tube on at least the portion of its inner surface facing an introduction bore in said graphite tube assembly.

8. A graphite tube assembly according to claim 1 wherein said inner body is of hollow cylindrical configuration and has a gas impermeable lining on at least the portion of its inner surface facing an introduction bore in said graphite tube assembly.

9. A graphite tube assembly according to claim 8 wherein said gas impermeable lining consists of a coating of pyrolytic graphite.

10. A graphite tube assembly according to claim 8 wherein said gas impermeable lining consists of metal.

11. A graphite tube assembly according to claim 10 wherein said gas impermeable lining consists of tungsten.

12. A graphite tube assembly according to claim 10 wherein said gas impermeable lining consists of tantalum.

13. A graphite tube assembly according to claim 10 wherein said gas impermeable lining is secured to the inner body by a shrink fit.

14. A graphite tube assembly according to claim 8 wherein said gas impermeable lining is a coating of ceramic material.

15. A graphite tube assembly according to claim 8 wherein said lining has grooves transversely disposed with respect to the axis of the graphite tube on at least the portion of its surface facing an introduction bore in said graphite tube assembly.

* * * * *